(12) United States Patent
Ohta et al.

(10) Patent No.: US 9,539,230 B2
(45) Date of Patent: Jan. 10, 2017

(54) COMPOSITION FOR REDUCING NEW-ONSET DIABETES

(71) Applicant: MOCHIDA PHARMACEUTICAL CO., LTD., Tokyo (JP)

(72) Inventors: Masahiko Ohta, Tokyo (JP); Shinichi Oikawa, Tokyo (JP); Mitsuhiro Yokoyama, Kobe (JP); Hideki Origasa, Toyama (JP); Masunori Matsuzaki, Ube (JP); Yuji Matsuzawa, Takaruzuka (JP); Yasushi Saito, Chiba (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/432,012

(22) PCT Filed: Sep. 19, 2013

(86) PCT No.: PCT/JP2013/075287
§ 371 (c)(1),
(2) Date: Mar. 27, 2015

(87) PCT Pub. No.: WO2014/050692
PCT Pub. Date: Apr. 3, 2014

(65) Prior Publication Data
US 2015/0250754 A1    Sep. 10, 2015

(51) Int. Cl.
*A61K 31/202* (2006.01)
*A61K 31/232* (2006.01)

(52) U.S. Cl.
CPC ......... *A61K 31/202* (2013.01); *A61K 31/232* (2013.01)

(58) Field of Classification Search
CPC .................... A61K 31/202; A61K 31/232
See application file for complete search history.

(56) References Cited

U.S. PATENT DOCUMENTS 5,760,081 A    6/1998 Leaf et al.

FOREIGN PATENT DOCUMENTS

| CN | 103054845 A | 4/2013 |
|---|---|---|
| EP | 1834639 A1 | 9/2007 |
| EP | 2022495 A1 | 2/2009 |
| EP | 2324827 A1 | 5/2011 |
| WO | WO 2010/147994 A1 | 12/2010 |

OTHER PUBLICATIONS

Saito et al. Atherosclerosis, (2008), 200(1), p. 135-140. (Cited in IDS).*
Sattar et al., Lancet, (2010), 375(9716), pp. 735-742. (Cited in IDS).*
Nobukata et al., Hetabolism, (2000), 49(7), pp. 912-919. (Cited in IDS).*
Carter et al., "Risk of incident diabetes among patients treated with statins: population based study", BMJ, May 23, 2013, vol. 346, No. f2610, pp. 1-11.
Full Prescribing Information of Crestor AstraZeneca, Revised Feb. 28, 2012.
Goldfine, "Statins: Is it Really Time to Reassess Benefits and Risks?", New Engl. J. Med., May 10, 2012, vol. 366, No. 19, pp. 1752-1755.
International Search Report, issued in PCT/JP2013/075287, mailed Dec. 10, 2013.
Naci et al., "Comparative Tolerability and Harms of Individual Statins: A Study-Level Network Meta-Analysis of 246 955 Participants From 135 Randomized Controlled Trials", Circ. Cardiovasc. Qual. Outcomes, Jul. 9, 2013.
Nobukata et al., "Long-Term Administration of Highly Purified Eicosapentaenoic Acid Ethyl Ester Prevents Diabetes and Abnormalities of Blood Coagulation in Male WBN/Kob Rats", Metabolism, Jul. 2000, vol. 49, No. 7, pp. 912-919.
Saito et al., "Effects of EPA on coronary artery disease in hypercholesterolemic patients with multiple risk factors: Sub-analysis of primary prevention cases from the Japan EPA Lipid Intervention Study (JELIS)", Atherosclerosis, 2008, vol. 200, No. 1, pp. 135-140.
Sattar et al., "Statins and risk of incident diabetes: a collaborative meta-analysis of randomised statin trials", Lancet, Feb. 27, 2010, vol. 375, No. 9716, pp. 735-742.
Extended European Search Report dated Feb. 22, 2016, for European Application No. 13840729.1.
Chinese Office Action and Search Report for Chinese Application No. 201380050656.8, dated May 5, 2016, with a partial English translation.

* cited by examiner

*Primary Examiner* — Yong Chu
(74) *Attorney, Agent, or Firm* — Birch, Stewart, Kolasch & Birch, LLP

(57) ABSTRACT

A medical composition for reducing the rate of new-onset diabetes caused by administration of a statin or for inhibiting an increase in blood glucose level by administration of a statin, the composition containing at least one ingredient selected from the group consisting of icosapentaenoic acid and pharmaceutically acceptable salts or esters thereof as an inactive ingredient.

14 Claims, 1 Drawing Sheet

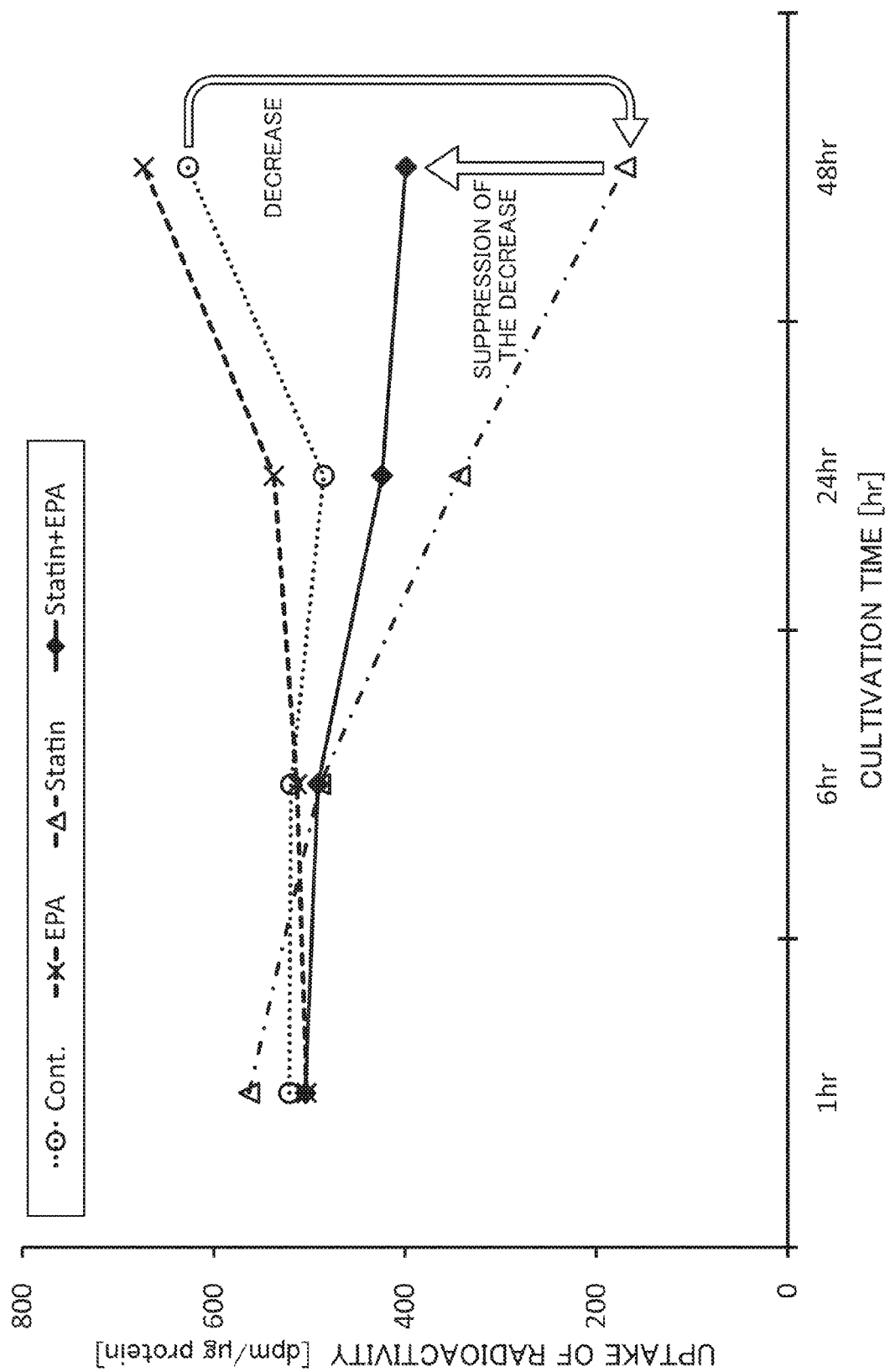

COMPOSITION FOR REDUCING NEW-ONSET DIABETES

TECHNICAL FIELD

This invention relates to a pharmaceutical composition for reducing new incidence rate of diabetes by statin administration.

BACKGROUND ART

Dyslipidemia is a large risk factor of arteriosclerosis, and arteriosclerosis is the cause of coronary artery diseases such as angina pectoris and myocardial infarction and cerebral stroke such as cerebral hemorrhage and cerebral infarction which are major death causes of Japanese. In the meanwhile, it has been demonstrated that these cardiovascular diseases can be prevented and treated by treating such dyslipidemia.

According to the diagnostic criteria of Atherosclerotic Diseases Prevention Guideline (2012), dyslipidemia is divided into hyper-LDL cholesterolemia (LDL cholesterol (hereinafter also referred to as "LDL-C") 140 mg/dL), borderline hyper-LDL-cholesterolemia (LDL-C, 120 to 139 mg/dL), low HDL cholesterolemia (HDL cholesterol (hereinafter also referred to as "HDL-C")<40 mg/dL), and hyper-triglyceridemia (triglyceride (hereinafter also referred to as "TG")≥150 mg/dL). Recently, the hyper-LDL cholesterolemia, the low HDL-cholesterolemia, and the hypertriglyceridemia are conceived as independent risk factors.

The therapeutic agent used for the dyslipidemia differs by the type of the dyslipidemia, and statin is the first choice for treating the hyper-LDL-cholesterolemia. Statin acts in mevalonic acid synthetic pathway wherein biosynthesis of isopentenyl diphosphoric acid and dimethyl allyl diphosphoric acid (starting materials of steroid synthesis) from acetyl CoA takes place by inhibiting HMG-CoA reductase (EC 1.1.1.34) (hereinafter also referred to as "HMG-CoA") which is an enzyme catalyzing the reaction of reducing hydroxymethyl glutaryl CoA to mevalonic acid, and thereby suppressing the biosynthesis of the cholesterol. The thus reduced cholesterol biosynthesis also invites effects such as enhanced expression of liver LDL (low density lipoprotein) receptor, increased incorporation of LDL-C from the blood into the liver, suppressed VLDL (very low density lipoprotein) secretion into the blood, and reduced serum TG and increased HDL-C. In view of such function of the statin, statin is also referred to as HMG-CoA reductase inhibitor (HMG-CoA RI).

Statin is effective for the treatment of cardiovascular diseases and prevention of cardiovascular events, and statin has been considered to be a safe drug with high tolerability. However, recent reports indicate relation between the statin and the risk of diabetes incidence. For example, Non-Patent Document 1 discloses that, in the general evaluation conducted by collecting the results of 16 clinical trials wherein participants were divided into the group administered with statin (lipid lowering drug) and the group not administered with the statin, the risk of diabetes incidence was 9% higher in the group administered with the statin. In addition, United States Food and Drug Administration announced a safety communication on the increase of blood glucose and risk of type 2 diabetes incidence by the statin administration in February, 2012, and the package insert of the statin preparation now includes the description that the statin administration invited an increase of hemoglobin A1c (hereinafter also referred to as "HbA1c") and fasting blood glucose and significant increase in the diabetes incidence (Non-Patent Document 2). However, it has been conceived, even if the risk of diabetes incidence should increase by the statin administration, the benefit of the reduced risk of the cardiovascular event incidence by the statin exceeds such risk and there is no reason for stopping the statin administration. On the other hand, it has also been conceived that the statin should be used with the monitoring of the blood glucose and the glycohemoglobin blood glucose in the case of patients with borderline blood glucose and the like suffering from high risk of diabetes incidence (Non-Patent Document 3).

Some reports examine relation between the type of statin and the risk of the diabetes incidence. For example, Non-Patent Document 4 evaluated new incidence of the diabetes in aged people of at least 66 years old administered with statin, and reports that the risk of the incidence of the diabetes significantly increased in the case of atorvastatin, rosuvastatin, and simvastatin compared to the case of pravastatin, and no significant difference was found in the case of fluvastatin and lovastatin. Non-Patent Document 5 describes that, in the meta-analysis of the tolerability and safety of the statin, the risk of the incidence of the diabetes increased by the statin administration while no difference was found by the type of the statin.

CITATION LIST

Non-Patent Literature

[Non-Patent Literature 1] Naveed Sattar et al. (2010) Statins and risk of incident diabetes: a collaborative meta-analysis of randomized statin trials. Lancet 375(9716): 735-742.

[Non-Patent Literature 2] FULL PRESCRIBING INFORMATION of CRESTOR, AstraZeneca, Revised 28th February, 2012.

[Non-Patent Literature 3] Allison B. Goldfine (2012) Statins: Is it really time to reassess benefits and risks? New Engl. J. Med. 366: 1752-1755.

[Non-Patent Literature 4] Aleesa A. Carter (2013) Risk of incident diabetes among patients treated with statins: population based study BMJ 346: f2610.

[Non-Patent Literature 5] Huseyin Naci (2013) Comparative Tolerability and Harms of Individual Statins: A Study-Level Network Meta-Analysis of 246955 Participants From 135 Randomized Controlled Trials. Circ. Cardiovasc. Qual. and Outcomes Jul. 9, 2013.

SUMMARY OF INVENTION

Technical Problem

Usefulness of the statin in treating the cardiovascular diseases and preventing the cardiovascular events is well recognized, and it has been difficult to stop the lipid control by the statin even if use of the statin involved an increase in the risk of diabetes incidence. Accordingly, there is a demand for suppressing increase of the blood glucose and new diabetes incidence in the patients administered with the statin, and in particular, in the patients with high risk of diabetes incidence such as patients having a border range blood glucose while continuing the dyslipidemia treatment by statin administration. The mechanism of the increase of the new diabetes incidence risk by statin, however, is yet unclear, and there has been so far no drug capable of reducing the new diabetes incidence risk in the patients administered with the statin. Accordingly, an object of the present invention is to provide a pharmaceutical composition for suppressing new incidence of diabetes of the patient administered with the statin. In the present invention, the term "diabetes" is used for type II diabetes unless otherwise noted.

Solution to Problems

The inventors of the present invention analyzed the trial data obtained in a large scale randomized controlled trial (Japan EPA Intervention Study (DELIS)) examining the effects of suppressing onset of the coronary artery events (primary prevention and secondary prevention) in Japanese hyperlipidemia patients administered with statin by long term administration of high purity EPA preparation, and for the first time found that the patients administered with the high purity EPA preparation exhibit no significant increase of the new incidence rate of the diabetes; and hence, that the new incidence rate of the diabetes is reduced in the patients administered with the statin by the administration of at least one member selected from the group consisting of icosapentaenoic acid and pharmaceutically acceptable salts and esters thereof (hereinafter also referred to as "EPA", and unless otherwise noted, this also applies to the following), and in particular ethyl icosapentate (hereinafter also referred to as "EPA-E"). The inventors of the present invention also found by an in vitro test using cultivated skeletal muscle cells that, while statin decreases glucose uptake by the skeletal muscle cells, the EPA suppresses such glucose uptake decrease by the skeletal muscle cell by statin, and hence, that the EPA is capable of suppressing the blood glucose increase by statin.

Accordingly, the present invention provides the pharmaceutical composition as described below.

(1) A pharmaceutical composition for reducing new incidence rate of diabetes due to administration of statin (HMG-CoA RI) containing at least one member selected from the group consisting of icosapentaenoic acid and its pharmaceutically acceptable salts and esters as its effective component.

(2) A pharmaceutical composition according to the above (1) which is administered to a patient having a serum HDL cholesterol concentration of less than 40 mg/dL.

(3) A pharmaceutical composition according to the above (1) which is administered to a low HDL cholesterolemia patient.

(4) A pharmaceutical composition according to the above (2) or (3) which is administered to a patient having a serum triglyceride concentration of at least 150 mg/dL.

(5) A pharmaceutical composition according to the above (2) or (3) which is administered to a hypertriglyceridemia patient.

(6) A pharmaceutical composition according to any one of the above (1) to (5) which is administered to a patient administered with HMG-CoA RI having a fasting blood glucose of less than 126 mg/dL.

(7) A pharmaceutical composition according to any one of the above (1) to (6) which is administered to a patient administered with HMG-CoA RI having a fasting blood glucose of at least 110 mg/dL and less than 126 mg/dL.

(8) A pharmaceutical composition according to any one of the above (1) to (6) which is administered to a patient administered with HMG-CoA RI having a fasting blood glucose of at least 100 mg/dL and less than 110 mg/dL.

(9) A pharmaceutical composition according to any one of the above (1) to (8) which is administered to a patient administered with HMG-CoA RI having impaired glucose tolerance or obesity.

(10) A pharmaceutical composition according to any one of the above (1) to (9) wherein at least one member selected from the group consisting of icosapentaenoic acid and its pharmaceutically acceptable salts and esters is ethyl icosapentate or icosapentaenoic acid (free acid).

(11) A pharmaceutical composition for suppressing increase of the blood glucose due to administration of statin (HMG-CoA RI) containing at least one member selected from the group consisting of icosapentaenoic acid and its pharmaceutically acceptable salts and esters as its effective component.

(12) A pharmaceutical composition according to the above (11) which is administered to a patient having a serum HDL cholesterol concentration of less than 40 mg/dL.

(13) A pharmaceutical composition according to the above (11) which is administered to a low HDL cholesterolemia patient.

(14) A pharmaceutical composition according to the above (12) or (13) which is administered to a patient having a serum triglyceride concentration of at least 150 mg/dL.

(15) A pharmaceutical composition according to the above (12) or (13) which is administered to a hypertriglyceridemia patient.

(16) A pharmaceutical composition according to any one of the above (11) to (15) which is administered to a patient administered with HMG-CoA RI having a fasting blood glucose of less than 126 mg/dL.

(17) A pharmaceutical composition according to any one of the above (11) to (16) which is administered to a patient administered with HMG-CoA RI having a fasting blood glucose of at least 110 mg/dL and less than 126 mg/dL.

(18) A pharmaceutical composition according to any one of the above (11) to (16) which is administered to a patient administered with HMG-CoA RI having a fasting blood glucose of at least 100 mg/dL and less than 110 mg/dL.

(19) A pharmaceutical composition according to any one of the above (11) to (18) which is administered to a patient administered with HMG-CoA RI having impaired glucose tolerance or obesity.

(20) A pharmaceutical composition according to any one of the above (11) to (19) wherein at least one member selected from the group consisting of icosapentaenoic acid and its pharmaceutically acceptable salts and esters is ethyl icosapentate or icosapentaenoic acid (free acid).

(21) A pharmaceutical composition according to any one of the above (1) to (20) wherein EPA content ratio in total fatty acid and its derivatives is at least 96.5% by weight.

(22) A pharmaceutical composition according to any one of the above (1) to (21) wherein the EPA is orally administered at a dose of 0.9 g/day to 2.7 g/day.

(23) A pharmaceutical composition according to any one of the above (1) to (22) wherein the EPA is administered at least for 2 years.

(24) A pharmaceutical composition according to any one of the above (1) to (23) wherein the composition is used in combination with HMG-CoA RI.

(25) A pharmaceutical composition according to any one of the above (1) to (24) wherein the composition contains the EPA and the HMG-CoA RI.

(26) A pharmaceutical composition according to any one of the above (1) to (25) wherein the composition is used in combination with a diet therapy.

(27) A pharmaceutical composition according to any one of the above (1) to (26) wherein the composition is capable of, in a patient administered with statin (HMG-CoA RI), reducing the incidence rate of the cardiovascular event, and in particular, incidence rate of the cardiovascular event that could not be prevented by the single administration of the HMG-CoA RI, or serum T-Cho concentration and/or serum TG concentration.

The present invention also provides the method as described below.

(28) A method for reducing new incidence rate of diabetes due to administration of HMG-CoA RI comprising the step of administering a pharmaceutical composition containing at least one member selected from the group consisting of icosapentaenoic acid and its pharmaceutically acceptable salts and esters as its effective component to a patient administered with statin (HMG-CoA RI).

(29) A method according to the above (28) wherein the patient has a serum HDL cholesterol concentration of less than 40 mg/dL.

(30) A method according to the above (28) wherein the patient simultaneously suffers from low HDL cholesterolemia.

(31) A method according to the above (29) or (30) wherein the patient has a serum triglyceride concentration of at least 150 mg/dL.

(32) A method according to the above (29) or (30) wherein the patient simultaneously suffers from hypertriglyceridemia.

(33) A method according to any one of the above (28) to (32) wherein the patient has a fasting blood glucose of less than 126 mg/dL.

(34) A method according to any one of the above (28) to (33) wherein the patient has a fasting blood glucose of at least 110 mg/dL and less than 126 mg/dL.

(35) A method according to any one of the above (28) to (33) wherein the patient has a fasting blood glucose of at least 100 mg/dL and less than 110 mg/dL.

(36) A method according to any one of the above (28) to (35) wherein the patient has impaired glucose tolerance or obesity.

(37) A method according to any one of the above (28) to (36) wherein at least one member selected from the group consisting of icosapentaenoic acid and its pharmaceutically acceptable salts and esters is ethyl icosapentate or icosapentaenoic acid (free acid).

(38) A method for suppressing increase of blood glucose due to administration of HMG-CoA RI comprising the step of administering a pharmaceutical composition containing at least one member selected from the group consisting of icosapentaenoic acid and its pharmaceutically acceptable salts and esters as its effective component to a patient administered with statin (HMG-CoA RI).

(39) A method according to the above (38) wherein the patient has a serum HDL cholesterol concentration of less than 40 mg/dL.

(40) A method according to the above (38) wherein the patient simultaneously suffers from low HDL cholesterolemia.

(41) A method according to the above (39) or (40) wherein the patient has a serum triglyceride concentration of at least 150 mg/dL.

(42) A method according to the above (39) or (40) wherein the patient simultaneously suffers from hypertriglyceridemia.

(43) A method according to any one of the above (38) to (42) wherein the patient has a fasting blood glucose of less than 126 mg/dL.

(44) A method according to any one of the above (38) to (43) wherein the patient has a fasting blood glucose of at least 110 mg/dL and less than 126 mg/dL.

(45) A method according to any one of the above (38) to (43) wherein the patient has a fasting blood glucose of at least 100 mg/dL and less than 110 mg/dL.

(46) A method according to any one of the above (38) to (45) wherein the patient has impaired glucose tolerance or obesity.

(47) A method according to any one of the above (38) to (46) wherein at least one member selected from the group consisting of icosapentaenoic acid and its pharmaceutically acceptable salts and esters is ethyl icosapentate or icosapentaenoic acid (free acid).

(48) A method for improving abnormal glucose tolerance or obesity of a patient administered with HMG-CoA RI having abnormal glucose tolerance or obesity comprising the step of administering a pharmaceutical composition containing at least one member selected from the group consisting of icosapentaenoic acid and its pharmaceutically acceptable salts and esters as its effective component to a patient administered with statin (HMG-CoA RI) having abnormal glucose tolerance or obesity.

(49) A method according to the above (48) wherein the patient has a serum HDL cholesterol concentration of less than 40 mg/dL.

(50) A method according to the above (48) wherein the patient simultaneously suffers from low HDL cholesterolemia.

(51) A method according to the above (49) or (50) wherein the patient has a serum triglyceride concentration of at least 150 mg/dL.

(52) A method according to the above (49) or (50) wherein the patient simultaneously suffers from hypertriglyceridemia.

(53) A method according to any one of the above (48) to (52) wherein the patient has a fasting blood glucose of less than 126 mg/dL.

(54) A method according to any one of the above (48) to (53) wherein the patient has a fasting blood glucose of at least 110 mg/dL and less than 126 mg/dL.

(55) A method according to any one of the above (48) to (53) wherein the patient has a fasting blood glucose of at least 100 mg/dL and less than 110 mg/dL.

(56) A method according to any one of the above (48) to (55) wherein at least one member selected from the group consisting of icosapentaenoic acid and its pharmaceutically acceptable salts and esters is ethyl icosapentate or icosapentaenoic acid (free acid).

(57) A method according to any one of the above (28) to (56) wherein EPA content ratio in total fatty acid and its derivatives is at least 96.5% by weight.

(58) A method according to any one of the above (28) to (57) wherein the EPA is orally administered at a dose of 0.9 g/day to 2.7 g/day.

(59) A method according to any one of the above (28) to (58) wherein the EPA is administered at least for 2 years.

(60) A method according to any one of the above (28) to (59) wherein the pharmaceutical composition is used in combination with HMG-CoA RI.

(61) A method according to any one of the above (28) to (60) wherein the composition contains the EPA and the HMG-CoA RI.

(62) A method according to any one of the above (28) to (61) wherein the composition is used in combination with a diet therapy.

(63) A method according to any one of the above (28) to (62) wherein the composition is capable of, in a patient administered with statin (HMG-CoA RI), reducing the incidence rate of the cardiovascular event, and in particular incidence rate of the cardiovascular event that could not be prevented by the single administration of the HMG-CoA RI, or serum T-Cho concentration and/or serum TG concentration.

(64) A method for advertising a pharmaceutical composition used in any one of the methods:

1) a method for reducing new incidence rate of diabetes due to administration of HMG-CoA RI, 2) a method for suppressing increase of blood glucose due to administration of the HMG-CoA RI, and 3) a method for improving abnormal glucose tolerance or obesity of a patient administered with HMG-CoA RI having abnormal glucose tolerance or obesity, which comprises the step of administering a pharmaceutical composition containing at least one member selected from the group consisting of icosapentaenoic acid and its pharmaceutically acceptable salts and esters as its effective component to a patient administered with statin (HMG-CoA RI).

The information on the method as described above of the present invention is provided to physicians and test participants. More specifically, such information is provided, for example, by the distribution of brochure or electric medium or by the provision of the information through the internet.

Advantageous Effects of Invention

The pharmaceutical composition of the present invention provides a means for reducing the new incidence rate of diabetes due to statin administration in the patients administered with statin (HMG-CoA RI). Of the patients administered with statin, the pharmaceutical composition of the present invention is particularly effective for those having higher risk of diabetes incidence. The pharmaceutical composition of the present invention also provides a means for suppressing increase of blood glucose due to statin administration in the patients administered with statin (HMG-CoA RI). Of the patients administered with statin, the pharmaceutical composition of the present invention is particularly effective for those who are susceptible to undergo blood glucose increase. Furthermore, the pharmaceutical composition of the present invention has high safety and reduced side effects.

The pharmaceutical composition of the present invention also provides a means for reducing the new incidence rate of diabetes due to statin administration and/or suppressing increase of blood glucose due to statin administration in the patients administered with statin (HMG-CoA RI), and in particular, a means for realizing effects such as the effect of preventing the incidence of cardiovascular events which could not be prevented by solely administering the HMG-CoA RI and the effect of reducing the serum T-Cho concentration and serum TG.

BRIEF DESCRIPTION OF DRAWING

FIG. 1 is a graph showing the effect of the statin and the EPA on glucose uptake by cultivated human rhabdomyosarcoma cell.

DESCRIPTION OF EMBODIMENTS

Next, the present invention is described in detail.
1. Pharmaceutical Composition
(1) Effective Components The pharmaceutical composition of the present invention contains at least one member selected from the group consisting of icosapentaenoic acid and its pharmaceutically acceptable salts and esters as its effective component.

Examples of the pharmaceutically acceptable salt include inorganic salts such as sodium salt and potassium salt, salts with an organic base such as benzylamine salt and diethylamine salt, and salts with a basic amino acid such as arginine salt and lysine salt.

Examples of the pharmaceutically acceptable ester include alkyl esters such as ethyl ester and glycerin ester such as mono-, di-, and tri-glycerides.

The EPA is preferably ethyl icosapentate (hereinafter also referred to as "EPA-E"), icosapentaenoic acid (free acid) or sodium eicosapentate (hereinafter also referred to as "EPA-Na"), and more preferably, EPA-E.

The EPA is not particularly limited for its purity. However, content of the EPA in the all fatty acids in the pharmaceutical composition of the present invention is typically at least 25% by weight, preferably at least 40% by weight, more preferably at least 50% by weight, still more preferably at least 70% by weight, still more preferably at least 85% by weight, still more preferably at least 96.5% by weight, and the most preferred is the embodiment wherein the composition is substantially free from the fatty acid other than the EPA.

When the at least one member selected from the group consisting of icosapentaenoic acid and its pharmaceutically acceptable salts and esters is EPA-E, content of the impurities which are unpreferable for cardiovascular events such as saturated fatty acid and arachidonic acid will be reduced, and the desired action and effect will be realized without the problems of excessive nutrition or excessive intake of vitamin A. Since EPA-E is an ester, it has a higher stability to oxidation compared to fish oils which mainly comprises a triglyceride, and a sufficiently stable composition will be produced by adding a commonly used antioxidant. The antioxidant added may be, for example, at least one antioxidant selected from butylated hydroxytoluene, butylated hydroxyanisole, propyl gallate, gallic acid, and pharmaceutically acceptable quinone and α-tocopherol, and such agent may be added at an effective amount.

When the at least one member selected from the group consisting of icosapentaenoic acid and its pharmaceutically acceptable salts and esters is EPA (free acid), content of the impurities which are unpreferable for cardiovascular events such as saturated fatty acid and arachidonic acid will be reduced, and the desired action and effect will be realized without the problems of excessive nutrition or excessive intake of vitamin A. In addition, since the EPA is a free acid, cleavage of ester bond by elastase is unnecessary in the absorption in the intestinal tract, and absorption higher than that of EPA-E or triglyceride form is expected particularly in the case of fasting administration. The antioxidant added may be, for example, at least one antioxidant selected from butylated hydroxytoluene, butylated hydroxyanisole, propyl gallate, gallic acid, and pharmaceutically acceptable quinone and α-tocopherol, and such agent may be added at an effective amount.

Exemplary dosage form of the preparation include oral administration to the patient in the form of tablet, capsule, microcapsule, granules, fine granules, powder, oral liquid preparation, emulsion, self-emulsifying preparation, syrup, and jelly, and the particularly preferred is oral administration by incorporating the composition in the capsule such as soft capsule or microcapsule. Exemplary EPA-E include a soft capsule containing high purity EPA-E (at least 96.5% by weight) (product name, Epadel, manufactured by Mochida Pharmaceutical Co., Ltd.) which are available in Japan as therapeutic agents for arteriosclerosis obliterans or hypertriglyceridemia, and a soft capsule containing high purity EPA-E (product name, Vascepa, manufactured by Amarin Pharma Inc.), a soft capsule containing about 46% by weight of EPA-E and about 38% by weight of DHA-E in the total fatty acid (Lovaza manufactured by GlaxoSmithKline and Omacor manufactured by ProNova Inc.), and a soft capsule containing 50 to 60% by weight of EPA (free acid) and 15 to 25% by weight of DHA (free acid) in the total fatty acid (Epanova manufactured by Omthera) which are approved in the U.S. as therapeutic agents for severe hypertriglyceridemia.

When the pharmaceutical composition of the present invention is orally administered, preferably 0.1 to 10 g/day, more preferably 0.3 to 6 g/day, still more preferably 0.6 to 4 g/day, and even more preferably 0.9 to 2.7 g/day of EPA-E is administered in 1 to 3 doses, and if necessary or if desired, the composition may be administered in 1 to several doses. The composition is preferably administered during or after the meal, and more preferably, immediately (within 30 minutes) after the meal. In the case of self-emulsifying preparation (for example, see WO 2010/134614) which exhibits high fasting absorption, the preparation may be administered not during the meal, after the meal, or immediately after the meal. The pharmaceutical composition of the present invention may also be used in combination with the diet therapy (for example, limitation of daily calorie, regular meal, balanced diet, balanced intake of nutritional elements (carbohydrate, protein, fat, mineral, vitamin, dietary fiber, and the like), etc.), and in such a case, daily dose, frequency, and/or timing of the administration can be adjusted as desired. The daily dose and frequency of the EPA (free acid) administration when the pharmaceutical composition of the present invention contains the EPA (free acid) may be determined by referring to the pharmaceutical composition containing EPA-E.

When the dose as described above is orally administered, the administration is preferably conducted while administering the statin. For example, the administration period is at least 1 year, preferably at least 2 years, more preferably at least 3 years, and still more preferably at least 5 years, and the administration is preferably continued while there is the risk of the incidence rate of new diabetes and/or blood glucose increase due to the statin administration is still present. If desired, drug withdrawal period of approximately 1 day to 3 months, and preferably approximately 1 week to 1 month may be included.

The administration period may be adequately set depending on the type of the disease to be treated and the degree of the symptom. For example, when the disease to be treated is dyslipidemia, the administration period is not particularly limited when the administration is conducted to achieve the effects of improving or treating dyslipidemia-related biochemical marker or pathologies or to suppress the progress into metabolic syndrome, cardio-cerebrovascular events, peripheral ulcer, gangrene, and the like. Exemplary conditions include improvement in the concentration of lipid markers in plasma (total cholesterol (hereinafter referred to as Cho), TG, TG after the meal, low density lipoprotein Cho, high density lipoprotein Cho, very low density lipoprotein Cho, non-high density lipoprotein Cho, intermediate density lipoprotein Cho, very high density lipoprotein Cho, free fatty acid, phospholipid, chylomicron, ApoB, lipoprotein (a), and remnant-like protein Cho, small dense low density lipoprotein Cho, etc.), increase in the peripheral skin temperature which can be measured by thermography or the like, increase in the walk distance, improvement of the test value such as serum creatinine phosphokinase, and improvement of symptoms such as numbness, coldness, pain, pain at rest, itching, cyanosis, redness, chilblain, neck stiffness, anemia, unhealthy complexion, pruritus, and crawling; and the administration may be conducted by monitoring improvement or therapeutic effects for these conditions. The administration may be conducted by monitoring the improvement or the therapeutic effects using other biochemical, pathological, or disease parameters. Desirably, the administration is continued while biochemical marker values such as plasma lipid concentration and abnormal pathology are still observed.

(2) Fatty Acid which May be Incorporated in Addition to the EPA

Examples of other fatty acids (not limited to free fatty acid and including pharmaceutically acceptable salts, esters, and other derivatives, and this also applies to the following description in this item) which may be incorporated include ω3 long chain unsaturated fatty acid, which is more preferably at least one member selected from the group consisting of docosahexaenoic acid, docosapentaenoic acid, and pharmaceutically acceptable salts and esters thereof (hereinafter also simply referred to as "DHA", and unless otherwise noted, this also applies to the following), and more preferably DHA, and still more preferably ethyl docosahexaenoate (hereinafter also referred to as "DHA-E").

When the pharmaceutical composition of the present invention contains EPA-E and DHA-E, the proportion of the total content of the EPA-E and the DHA-E in the total fatty acid content of the pharmaceutical composition of the present invention is not particularly limited. The proportion, however, is preferably at least 40% by weight, more preferably at least 60% by weight, still more preferably at least 80% by weight, and still more preferably at least 90% by weight, and the most preferred is the embodiment wherein the fatty acid other than the ω3 long chain unsaturated fatty acid is substantially absent. In other words, purity of the ω3 long chain unsaturated fatty acid in all fatty acids is preferably high, and more preferably, purity of the EPA and the DHA which are ω3 long chain unsaturated fatty acids is high, and still more preferably, purity of the EPA is high. For example, when the pharmaceutical composition of the present invention contains the EPA-E and the DHA-E, the ratio of the content of the EPA-E to the DHA-E (EPA-E/DHA-E) in all fatty acids of the pharmaceutical composition of the present invention is not particularly limited, and the ratio is preferably at least 0.8, more preferably at least 1.0, and more preferably at least 1.2. When the pharmaceutical composition of the present invention contains the EPA (free acid) and the DHA (free acid), total proportion of the EPA (free acid) and the DHA (free acid) in all fatty acids in the pharmaceutical composition of the present invention and the ratio of the EPA (free acid) to the DHA (free acid) (EPA/DHA) in all fatty acids in the pharmaceutical composition of the present invention corresponds to those of the pharmaceutical composition containing the EPA-E and the DHA-E.

When the pharmaceutical composition of the present invention contains EPA-E and the DHA-E, the daily dose of the EPA-E and the DHA-E which is not particularly limited is preferably 0.3 to 10 g/day, more preferably 0.5 to 6 g/day, and still more preferably 1 to 4 g/day as the total of the EPA-E and DHA-E, and if necessary or if desired, the composition may be administered in 1 to several doses. The composition is preferably administered during or after the meal, and more preferably, immediately (within 30 minutes) after the meal. In the case of self-emulsifying preparation (for example, see WO 2010/134614) which exhibits high fasting absorption, the preparation may be administered not during the meal, after the meal, or immediately after the meal. The pharmaceutical composition of the present invention may also be used in combination with the diet therapy, and in such a case, daily dose, frequency, and/or timing of the administration can be adjusted as desired. The daily dose and frequency of the EPA (free acid) and and DHA (free acid) administration when the pharmaceutical composition of the present invention contains the EPA (free acid) and DHA (free acid) may be determined in consideration of the corresponding case of the pharmaceutical composition containing EPA-E and DHA-E as described above.

When the dose as described above is administered, the administration period is preferably during the administration of the statin. For example, the administration period is at least 1 year, preferably at least 2 years, more preferably at least 3 years, and still more preferably at least 5 years, and the administration is preferably continued while there is the risk of the incidence rate of new diabetes and/or blood glucose increase due to the statin administration is still present. If desired, drug withdrawal period of approximately 1 day to 3 months, and preferably approximately 1 week to 1 month may be included.

The administration period may be adequately set depending on the type of the disease to be treated and the degree of the symptom. For example, when the disease to be treated is dyslipidemia, the administration period is not particularly limited when the administration is conducted to achieve the effects of improving or treating dyslipidemia-related biochemical marker or pathologies or to suppress the progress into metabolic syndrome, cardio-cerebrovascular events, peripheral ulcer, gangrene, and the like. Exemplary conditions include improvement in the concentration of lipid markers in plasma (total cholesterol (hereinafter referred to as Cho), TG, TG after the meal, low density lipoprotein Cho, high density lipoprotein Cho, very low density lipoprotein Cho, non-high density lipoprotein Cho, intermediate density lipoprotein Cho, very high density lipoprotein Cho, free fatty acid, phospholipid, chylomicron, ApoB, lipoprotein (a), and remnant-like protein Cho, small dense low density lipoprotein Cho, etc.), increase in the peripheral skin temperature which can be measured by thermography or the like, increase in the walk distance, improvement of the test value such as serum creatinine phosphokinase, and improvement of symptoms such as numbness, coldness, pain, pain at rest, itching, cyanosis, redness, chilblain, neck stiffness, anemia, unhealthy complexion, pruritus, and crawling; and the administration may be conducted by monitoring improvement or therapeutic effects for these conditions. The administration may be conducted by monitoring the improvement or the therapeutic effects using other biochemical, pathological, or disease parameters. Desirably, the administration is continued while biochemical marker values such as plasma lipid concentration and abnormal pathology are still observed.

Preferably, content of the long chain unsaturated fatty acids other than the EPA and the DHA is minimized as far as possible, and in particular, content of the ω6 long chain unsaturated fatty acids, and in particular, arachidonic acid should be minimized as far as possible, and the content is preferably less than 2% by weight, more preferably less than 1% by weight, still more preferably less than 0.5% by weight, and the most preferable is the embodiment wherein the ω6 long chain unsaturated fatty acid is substantially absent.

(3) Use in Combination with Statin

The pharmaceutical composition of the present invention is used in combination with the statin.

The "use in combination with the statin" includes both a simultaneous administration of the composition containing the EPA as its effective component with the statin and separate administration of such composition with the statin.

In the case of simultaneous administration, the pharmaceutical composition of the present invention and the statin may be formulated as a combined drug, a kit comprising the combination of these two drugs, or two separate drugs.

In the case of separate administration, the pharmaceutical composition of the present invention and the statin may be used at an adequate dose and ratio.

In addition, in the case of separate administration, the EPA may be administered either before or after the HMG-CoA RI. When these drugs are administered at different timings, the drugs may be administered, for example, by first administering one of the drugs and then administering the other drug at the timing when the effects of the first drug starts to be developed or during the full development of such effect for the action of the second drug. In other cases, one drug may be prepared in the form of a controlled-release drug and administered once a day, and the other drug may be administered two or more times, for example, twice or three times a day, or once a day as in the case of the first drug. The administration of both drugs once a day, or simultaneous administration both drugs once a day, or use of a preparation containing both drugs is preferable due to the reduced participant's burden of taking the drugs, and such administration is expected to result in the improved compliance and improved preventive/ameliorating or treating effects as well as improved effect of reducing the side effects. Alternatively, both drugs may be administered and the administration of one of the drugs may be stopped when the effects of the first drug starts to be developed or during the full development of such effect. In stopping the drug administration, the drug dose may be incrementally reduced. Furthermore, one of the drugs may be administered during drug withdrawal period of the other drug.

The "use in combination" is not necessarily limited to the cases of simultaneous presence in body, for example, in blood of the participants. The "use in combination" as used in the present invention however refers to the embodiment of the drug use wherein one of the drugs is administered while the action or the effect of the other drug is still expressed in the body of the patient.

The action mechanism how the new incidence rate of the diabetes due to statin is reduced or the increase of the blood glucose due to statin is suppressed by the pharmaceutical composition of the present invention in the patients administered with the statin not fully elucidated. Since EPA suppresses the decrease of the glucose take up by skeletal muscle cell by the statin, there is a possibility that EPA is suppressing the increase of the blood glucose due to statin. Suppressing of the blood glucose increase should result in the decrease of the risk of the diabetes incidence.

Furthermore, the pharmaceutical composition of the present invention is known to have the action of preventing the incidence of cardiovascular events, and in particular, the cardiovascular events which cannot be prevented by the single administration of the HMG-CoA RI as well as the action of reducing the serum T-Cho concentration and serum TG in the hyperlipidemia patients administered with the statin (HMG-CoA RI). Accordingly, increase of the new diabetes incidence rate and/or the blood glucose due to the statin administration will be suppressed, the incidence of cardiovascular events, and in particular, the cardiovascular events which cannot be prevented by the single administration of the HMG-CoA RI will be prevented, and the serum T-Cho concentration and serum TG will be reduced in the patients administered with statin (HMG-CoA RI).

2. Diabetes (1) Diagnostic Criteria of Diabetes

In the present invention, the patient who was at least once observed to have the fasting blood glucose of 126 mg/dL or higher is recognized as a patient suffering from diabetes.

It is to be noted that, in the clinical diagnostic criteria of the diabetes, a patient is diagnosed as diabetes when a) both blood glucose and HbA1c are diabetic in the initial examination (preferably measured on the same day, and this applies to the following), b) only blood glucose is diabetic in the initial examination, and typical diabetic symptoms or accurate diabetic retinopathy is found in the initial test, c) only blood glucose is diabetic in the initial examination, and both typical diabetic symptoms and accurate diabetic retinopathy are absent, and the blood glucose and/or the HbA1c is diabetic in the reexamination, and d) HbA1c is diabetic in the initial examination, and both blood glucose and HbA1c are diabetic, or only the blood glucose is diabetic in the reexamination.

(2) New Incidence and New Incidence Rate of the Diabetes

In the present invention, the term "new incidence of the diabetes" is used when a fasting blood glucose of 126 mg/dL or higher is measured at least once in the patient who has never been diagnosed as diabetes, and preferably in the patient who has no experience of the measurement of 126 mg/dL or higher.

The "new incidence rate of the diabetes" is percentage of the number of patient who has experienced the new incidence of the diabetes in the number of all patients administered with HMG-CoA RI.

3. Patients Who are Subject to the Administration of the Pharmaceutical Composition of the Present Invention (1) The Pharmaceutical Composition for Reducing the New Diabetes Incidence The patients subject to the administration of the pharmaceutical composition of the present invention for reducing the new incidence of the diabetes due to the administration of statin are not particularly limited as long as the patient is administered with the statin (HMG-CoA RI) and the patient has no experience of the incidence of the diabetes. Such patients are preferably those who have not experienced the incidence of the diabetes but who have higher risk of incidence since the effect of the pharmaceutical composition of the present invention to reduce the new diabetes incidence due to statin is more significant in patients who have higher risk of diabetes incidence.

Exemplary patients who have higher risk of diabetes incidence include those who are suffering from hyper-LDL-cholesterolemia or borderline hyper-LDL-cholesterolemia simultaneously with preferably low HDL-cholesterolemia, and more preferably low HDL-cholesterolemia and hypertriglyceridemia. It is to be noted that the diagnostic criteria of the hyper-LDL-cholesterolemia, the borderline hyper-LDL-cholesterolemia, the low HDL-cholesterolemia, and the hypertriglyceridemia are respectively serum LDL-C equal to or greater than 140 mg/dL, serum LDL-C of 120 to 139 mg/dL, serum HDL-C of less than 40 mg/dL, and serum TG equal to or greater than 150 mg/dL. These diagnostic criteria, however, are preferably renewed when the diagnostic criteria is revised.

Another group of patients who have higher risk of diabetes incidence is, for example, patients whose fasting blood glucose is in the borderline range or at a normal high value. The "borderline range" is the fasting blood glucose of at least 110 mg/dL and less than 126 mg/dL, and the "normal high value" is the fasting blood glucose of at least 100 mg/dL and less than 110 mg/dL. However, these thresholds are preferably renewed when the thresholds are revised.

Another group of patients who have higher risk of diabetes incidence is, for example, patients who are suffering from impaired glucose tolerance or obesity. The patients who are suffering from impaired glucose tolerance or obesity are conceived to be those having higher risk of diabetes incidence compared to the patients who are not suffering from the impaired glucose tolerance or obesity.

In the present invention, "impaired glucose tolerance" means that the value at 2 hours in OGTT (75 g oral glucose tolerance test) is neither normal type nor diabetes type. The 2 hour OGTT value is normal type when the 2 hour OGTT value is less than 140 mg/dL, and the 2 hour OGTT value is diabetes type when the 2 hour OGTT value is 200 mg/dL or higher.

In the present invention, "obesity" means the state of excessive adipose tissue accumulation. While the criteria may vary by the country, the term "obesity" is determined by the diagnostic criteria of Japan Society for the Study of Obesity, namely, the body-mass index (hereinafter, also referred to as "BMI") of at least 25.

(2) The Pharmaceutical Composition for Suppressing the Increase of the Blood Glucose The patients subject to the administration of the pharmaceutical composition of the present invention for suppressing the increase of the blood glucose due to the administration of statin are not particularly limited as long as the patient is administered with statin (HMG-CoA RI). Such patients are preferably those who have not experienced the incidence of the diabetes, and more preferably, those who have not experienced the incidence of the diabetes but who are susceptible to experience increase in the blood glucose since the effect of the pharmaceutical composition of the present invention to suppress the increase of the blood glucose due to statin is more significant in patients who are susceptible to experience increase in the blood glucose.

Exemplary patients who are susceptible to experience increase of the blood glucose include those who are suffering from hyper-LDL-cholesterolemia or borderline hyper-LDL-cholesterolemia simultaneously with preferably low HDL-cholesterolemia, more preferably low HDL-cholesterolemia and hypertriglyceridemia. It is to be noted that the diagnostic criteria of the hyper-LDL-cholesterolemia, the borderline hyper-LDL-cholesterolemia, the low HDL-cholesterolemia, and the hypertriglyceridemia are respectively serum LDL-C equal to or greater than 140 mg/dL, serum LDL-C of 120 to 139 mg/dL, serum HDL-C of less than 40 mg/dL, and serum TG equal to or greater than 150 mg/dL. These diagnostic criteria, however, are preferably renewed when the diagnostic criteria is revised.

Another group of patients who are susceptible to experience increase of the blood glucose is, for example, patients whose fasting blood glucose is in the borderline range or at a normal high value. The "borderline range" is the fasting blood glucose of at least 110 mg/dL and less than 126 mg/dL, and the "normal high value" is the fasting blood glucose of at least 100 mg/dL and less than 110 mg/dL. These thresholds, however, are preferably renewed when the thresholds are revised.

Another group of patients who are susceptible to experience increase of the blood glucose is, for example, patients who are suffering from impaired glucose tolerance or obesity. The patients who are suffering from impaired glucose tolerance or obesity are conceived to be those having higher risk of diabetes incidence compared to the patients who are not suffering from the impaired glucose tolerance or obesity.

In the present invention, "impaired glucose tolerance" means that the value at 2 hours in OGTT (75 g oral glucose tolerance test) is neither normal type nor diabetes type. The 2 hour OGTT value is normal type when the 2 hour OGTT value is less than 140 mg/dL, and the 2 hour OGTT value is diabetes type when the 2 hour OGTT value is 200 mg/dL or higher.

In the present invention, "obesity" means the state of excessive adipose tissue accumulation. While the criteria may vary by the country, the term "obesity" is determined by the diagnostic criteria of Japan Society for the Study of Obesity, namely, the BMI of at least 25.

(3) Statin

The statin (HMG-CoA RI) is not particularly limited as long as it is a drug which inhibits HMG-CoA reductase, and examples include atorvastatin, simvastatin, cerivastatin, fluvastatin, pravastatin, rosuvastatin, pitavastatin, lovastatin, and their pharmaceutically acceptable salts. Exemplary commercially available products include atorvastatin calcium (product name, Lipitor, Astellas Pharma/Pfizer Inc.), simvastatin (product name, Lipovas, MSD), cerivastatin sodium, fluvastatin sodium (product name, Lochol, Novartis Pharma), pravastatin sodium (product name, Mevalotin, Daiichi Sankyo), rosuvastatin calcium (product name, Crestor, Shionogi), pitavastatin calcium (product name, Livalo, Kowa), and lovastatin (product name, Mevacor, MSD). The term "statin" and "HMG-CoA RI" as used herein in relation to the pharmaceutical composition of the present invention include all of those as mentioned above.

The type of statin is not particularly limited. However, combination with a statin which is highly effective for reducing the cardiovascular risk is preferable since the statin which is highly effective for reducing the cardiovascular risk is also likely to have a high risk of diabetes incidence. For example, the preferred are atorvastatin, rosuvastatin, and simvastatin, and the more preferred are atorvastatin and rosuvastatin. The most preferred is atorvastatin.

Statin is preferably used by the prescribed method and at the prescribed dose, and the dose may be adjusted depending on the type, dosage form, administration route and daily frequency of the statin, degree of the symptom, body weight, sex, age, and the like. In the case of oral administration, 0.05 to 200 mg/day, and preferably 0.1 to 100 mg/day of statin may be administered at once or in two divided doses, and if desired, total dose may be administered in several divided doses. The dose may be reduced depending on the amount of the EPA-E administered.

It is to be noted that daily dose is preferably 5 to 60 mg, and more preferably 10 to 20 mg in the case of sodium pravastatin; preferably 2.5 to 60 mg, and more preferably 5 to 20 mg in the case of simvastatin; preferably 10 to 180 mg, and more preferably 20 to 60 mg in the case of fluvastatin sodium; preferably 5 to 120 mg, and more preferably 10 to 40 mg in the case of atorvastatin calcium hydrate; preferably 0.5 to 12 mg, and more preferably 1 to 4 mg in the case of pitavastatin calcium; preferably 1.25 to 60 mg, and more preferably 2.5 to 20 mg in the case of rosuvastatin calcium; preferably 5 to 160 mg, and more preferably 10 to 80 mg in the case of lovastatin; and preferably 0.075 to 0.9 mg, and more preferably 0.15 to 0.3 mg in the case of cerivastatin sodium; although the dose is not limited to those as described above.

The pharmaceutical composition and the method of the present invention may be used by incorporating other drug in addition to the EPA. The additional drug used in the present invention is not particularly limited as long as it does not adversely affect the merit of the present invention, and exemplary such drugs include hypoglycemic/antidiabetic, lipid-lowering drug, antihypertensive, antioxidant, and anti-inflammatory agent.

Exemplary hypoglycemic/antidiabetic drugs include α-glucosidase inhibitors such as acarbose, voglibose, and miglitol, sulfonyl urea hypoglycemics such as gliclazide, glibenclamide, glimepiride, and tolbutamide, rapid-acting insulin secretagogues such as nateglinide, repaglinide, and mitiglinide, biguanide hypoglycemics such as metformin hydrochloride, and buformin hydrochloride, dipeptidyl phosphatase 4 inhibitors such as sitagliptin, vildagliptin, alogliptin, and saxagliptin, thiazolidine drugs such as pioglitazone hydrochloride and rosiglitazone maleate, glucagon-like peptide 1 derivatives such as exenatide and liraglutide, insulin, and insulin derivatives.

Exemplary lipid-lowering drugs include fibrate drugs such as simfibrate, clofibrate, clinofibrate, bezafibrate, and fenofibrate, and lipase inhibitors such as orlistat and cetilistat, resins such as cholestyramine and colestimide, and ezetimibe.

Exemplary antihypertensives include angiotensin II receptor blockers such as irbesartan, olmesartan medoxomil, candesartan cilexetil, telmisartan, valsartan, losartan potassium, angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate, calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine, α blockers such as tolazoline and phentolamine, β blockers such as atenolol, metoprolol, acebutolol, propranolol, pindolol, carvedilol, and labetalol hydrochloride, α stimulants such as clonidine and methyldopa, and diuretics such as eplerenone, hydrochlorothiazide, and furosemide.

Exemplary antioxidants include vitamins such as ascorbic acid (vitamin C), tocopherol (vitamin E), and tocopherol nicotinic acid ester, N-acetyl cysteine, and probucol.

Exemplary anti-inflammatory agents include cytokine production inhibitor such as pentoxifylline, leukotriene receptor antagonist, leukotriene biosynthesis inhibitor, NSAIDs, COX-2 selective inhibitor, M2/M3 antagonist, steroids such as corticosteroid and prednisolone farnesylate, Hi (histamine) receptor antagonist, aminosalicylic acids such as salazosulfapyridine and mesalazine. Exemplary immunosuppressants include azathioprine, 6-mercaptoprine, and tacrolimus. Exemplary antiviral agents for hepatitis C virus (HCV) include interferon, protease inhibitor, helicase inhibitor, and polymerase inhibitor.

EXAMPLES

Suppression of the New Incidence of Diabetes in Patients Administered with HMG-CoA RI by EPA Administration The test data obtained in DELIS (Japan EPA Lipid Intervention Study) which is a large-scale randomized comparative test conducted since 1996 was examined for examining the effect of suppressing the incidence (primary and secondary prevention) of the coronary artery event induced by long-term administration of high purity EPA preparation in Japanese hyperlipidemia patients 1. Summary of the DELIS Test (1) Subjects Hyperlipidemia patients with serum total cholesterol of at least 250 mg/dL (men aged 40 to 75 years and postmenopausal women aged up to 75 years with serum total cholesterol of at least 250 mg/dL) were eligible for the study, and a total of 18,645 cases (14,981 primary prevention cases, 3,664 secondary prevention cases) were studied.

(2) Test Method

The hyperlipidemia patients were divided into 2 groups, namely, the control group (9,319 cases, the group with no EPA administration) and EPA group (9,326 cases), and the EPA group was administered with 1800 mg/day of high purity EPA preparation. Simultaneously, both groups were administered with statin (10 to 20 mg/day of pravastatin sodium, 5 to 10 mg/day of simvastatin, or 10 to 20 mg/day of atorvastatin calcium in terms of atorvastatin). The groups were followed for about 5 years, and evaluation was conducted. It is to be noted that the hyperlipidemia patients in the DELIS test were those having the serum total cholesterol (TC) concentration of at least 250 mg/dL including the patients whose serum TC concentration would be at least 250 mg/dL if the lipid was not controlled.

2. Analysis of New Incidence of Diabetes (1) Subject 15,605 cases without definite diagnosis of the diabetes (EPA group, 7,810 cases; control group 7,795 cases) were extracted from 18,645 cases registered in DELIS, and these cases were designated "group 1". As a consequence, 3,040 cases with definite diagnosis of the diabetes (not limited to Type 2 diabetes and including all types) were excluded from the entire registered cases.

Next, 15,311 cases including the cases with the fasting blood glucose of less than 126 mg/dL and the cases wherein the fasting blood glucose had not been measured (EPA group, 7,650 cases; control group, 7,661 cases) were extracted from group 1, and this group was designated "group 2". As a consequence, 294 cases with the blood glucose at the time of registration of at least 126 mg/dL were excluded from the group 1.

Next, 7,875 cases including the cases wherein the fasting blood glucose had been measured at least once in the observation period (EPA group, 3,976 cases; control group, 3,899 cases) were extracted from group 2, and this group was designated "group 3". As a consequence, 7,436 cases wherein the fasting blood glucose was not at all measured in the observation period were excluded from the group 2.

Furthermore, the cases wherein the serum HDL-C concentration was less than 40 mg/dL with no limitation in the serum TG were extracted from each of the group 1, group 2, and group 3, and this group was designated subgroup "HDL-C<40, no limitation in TG", and the cases wherein the serum HDL-C concentration was less than 40 mg/dL and the serum TG was at least 150 mg/dL were extracted from each of the group 1, group 2, and group 3, and this group was designated subgroup "HDL-C<40 and TG≥150"

The number of patients who experienced new incidence of the diabetes (DM: Diabetes Mellitus) during the DELIS test (number of DM incidence), proportion of such patients (DM incidence rate, %), and the suppression rate of DM incidence by EPA administration (%) are shown in Table 1.

TABLE 1

Number of patients experiencing new incidence and new incidence rate of Diabetes Mellitus

| Serum lipid [mg/dL] | | | HDL-C TG | No limitation on HDL-C and TG | HDL-C < 40 No limitation on TG | HDL-C < 40 TG ≥ 150 |
|---|---|---|---|---|---|---|
| Group 1 | EPA group | Total number | | 7810 | 620 | 501 |
| | | DM | Incidence number | 259 | 24 | 22 |
| | | | Incidence rate | 3.3% | 3.9% | 4.4% |
| | Control group | Total number | | 7795 | 642 | 523 |
| | | DM | Incidence number | 242 | 39 | 34 |
| | | | Incidence rate | 3.1% | 6.1% | 6.5% |
| | Suppression rate of DM incidence | | | −6.8% | 36.3% | 32.5% |
| Group 2 | EPA group | Total number | | 7650 | 608 | 486 |
| | | DM | Incidence number | 219 | 22 | 20 |
| | | | Incidence rate | 2.9% | 3.6% | 4.1% |
| | Control group | Total number | | 7661 | 637 | 514 |
| | | DM | Incidence number | 203 | 35 | 32 |
| | | | Incidence rate | 2.6% | 5.5% | 6.2% |
| | Suppression rate of DM incidence | | | −8.0% | 34.1% | 33.9% |
| Group 3 | EPA group | Total number | | 3976 | 295 | 239 |
| | | DM | Incidence number | 213 | 21 | 19 |
| | | | Incidence rate | 5.4% | 7.1% | 7.9% |

TABLE 1-continued

Number of patients experiencing new incidence
and new incidence rate of Diabetes Mellitus

| Serum lipid [mg/dL] | | | No limitation on HDL-C and TG | HDL-C < 40 No limitation on TG | HDL-C < 40 TG ≥ 150 |
|---|---|---|---|---|---|
| | HDL-C | | | | |
| | TG | | | | |
| Control group | Total number | | 3899 | 325 | 273 |
| | DM | Incidence number | 201 | 35 | 32 |
| | | Incidence rate | 5.2% | 10.8% | 11.7% |
| Suppression rate of DM incidence | | | −3.9% | 33.9% | 32.2% |

Furthermore, the cases wherein the fasting blood glucose was at least 110 mg/dL and less than 126 mg/dL were extracted from the subgroup "HDL-C<40, no limitation in TG" and the subgroup "HDL-C<40 and TG 150" of the group 3, and the number of DM incidence, the DM incidence rate, and the suppression rate of DM incidence are shown in Table 2.

TABLE 2

Number of patients experiencing new incidence
and new incidence rate of Diabetes Mellitus

| Fasting blood glucose (FPG) [mg/dL] | | | 110 ≤ FPG < 126 HDL-C < 40 | 110 ≤ FPG < 126 HDL-C < 40 |
|---|---|---|---|---|
| Serum lipid [mg/dL] | HDL-C | | No limitation on TG | HDL-C < 40 TG ≥ 150 |
| | TG | | | |
| Group 3 | EPA group | Total number | 25 | 19 |
| | | DM Incidence number | 4 | 3 |
| | | Incidence rate | 16.0% | 15.8% |
| | Control group | Total number | 19 | 17 |
| | | DM Incidence number | 5 | 5 |
| | | Incidence rate | 26.3% | 29.4% |
| Suppression rate of DM incidence | | | 39.2% | 46.3% |

It is to be noted that the incidence of the DM in Tables 1 and 2 means the new incidence of the DM, namely, the measurement of the fasting blood glucose of 126 mg/dL or higher in the patient who has never been diagnosed as diabetes, and preferably in the patient who has no experience of the measurement of 126 mg/dL or higher.

The overall results shown in Tables 1 and 2 were generally summarized, and the following suppressive effects by EPA may be expected as the effect of suppressing the new incidence of diabetes due to statin administration:

(1) suppression of about 34 to 36% in the patients with the HDL-C of less than 40 mg/dL,
(2) suppression of about 32 to 35% in the patients with the HDL-C of less than 40 mg/dL and the TG of 150 mg/dL or higher,
(3) suppression of about 39% in the patients with the fasting blood glucose of at least 110 mg/dL and less than 126 mg/dL and the HDL-C of less than 40 mg/dL, and
(4) suppression of about 46% in the patients with the fasting blood glucose of at least 110 mg/dL and less than 126 mg/dL, the HDL-C of less than 40 mg/dL, and the TG of at least 150 mg/dL.

[Suppression by EPA of the Decrease of Glucose Uptake by Skeletal Muscle Cells Induced by Statin]

1. Materials and Methods (1) Human fetal rhabdomyosarcoma cell line (RD cell, ATCC) was inoculated in 24 well plate and cultured in a growth medium (10% fetal bovine serum (FCS), Dulbecco's modified Eagle medium (DMEM), low glucose, 1% nonessential amino acid) to confluency.

(2) The cells were then cultivated in differentiation medium (2% horse serum (HS), Dulbecco's modified Eagle medium (DMEM), low glucose, 1% nonessential amino acid) for 3 to 5 days for differentiation into muscle cell.

(3) The cells were then cultivated in the differentiation medium supplemented with 0.5% of bovine serum albumin (BSA) (hereinafter referred to as "differentiation medium (0.5% BSA)"), the differentiation medium (0.5% BSA) supplemented with 30 μM of statin (simvastatin), the differentiation medium (0.5% BSA) supplemented with 50 μM of EPA (sodium eicosapentate), or the differentiation medium (0.5% BSA) supplemented with 50 μM of EPA (sodium eicosapentate) and 30 μM of statin (simvastatin) for 1 hr, 6 hr, 24 hr, or 48 hr.

The differentiation medium (0.5% BSA) supplemented with neither statin nor EPA was used for the control group (Cont.), the one supplemented only with the 30 μM of statin (simvastatin) was used as "statin group (Statin)", the one supplemented only with the 50 μM of EPA (sodium eicosapentate) was used as "EPA group (EPA)", and the one supplemented with both the 30 μM of statin (simvastatin) and the 50 μM of EPA was used as "statin+EPA group (Statin+EPA)".

(3) After the incubation, the medium was removed by aspiration, and the cells were incubated in an uptake buffer (140 mM NaCl, 5 mM KCl, 2.5 mM $MgSO_4$, 20 mM HEPES, 1 mM $CaCl_2$, pH=7.4) supplemented with 10 μM of 2-3H-deoxyglucose at 37° C. for 12 minutes.

(4) After the incubation, the cells were washed 4 times with cold stop solution (PBS(−)supplemented with 10 mM glucose,).

The PBS(−) contained 0.2 g of $NaH_2PO_4.2H_2O$, 3.225 g of $Na_2HPO_4.12H_2O$, and 8 g of NaCl in 1 L, and the pH was at 7.2 to 7.4.

(5) After the washing, 500 μL/well of aqueous solution of 0.4N sodium hydroxide was added, and the cells were lyzed by heating to 56° for 20 minutes.

(6) 300 μL of the well content (cell lysate) was mixed with 4 mL of Atomlight (manufactured by PerkinElmer), and $^3$H count was measured with a liquid scintillation counter. The well content (cell lysate) was also measured for its protein concentration to calculate the $^3$H count per 1 μg of the protein.

2. Results and Analysis (1) Uptake of Radioactivity

Table 3 shows radioactivity per 1 μg of protein (unit: dpm/μg protein) measured by using the liquid scintillation counter. FIG. 1 is the graph showing the uptake of radioactivity (y axis) in relation to the incubation time (x axis) for each group.

TABLE 3

| Uptake of radioactivity | | | | |
|---|---|---|---|---|
| Incubation time [hr] | 1 | 6 | 24 | 48 |
| Cont. | 521 | 519 | 485 | 627 |
| EPA | 503 | 513 | 537 | 673 |
| Statin | 563 | 489 | 343 | 170 |
| Statin + EPA | 504 | 491 | 424 | 399 |

Unit: dpm/μg protein (2) Effects of Statin

In the statin group (Statin), the uptake of the radioactivity is little different from that of the control group (Cont.) within 6 hr of cultivation. However, the radioactivity uptake drastically decreased at 24 hr and 48 hr of cultivation, and the rate of decrease at 48 hr of incubation was about 73%. In summary, the glucose uptake ability by the skeletal muscle cell decreases in the presence of statin.

This result indicates that the glucose uptake ability by the skeletal muscle cell in the patients administered with statin is impaired and they are in the condition of tendency of the blood glucose increase.

(3) Effects of EPA

In the EPA group (EPA), the uptake of the radioactivity tends to keep up with that of the control group (Cont.). However, the radioactivity uptake somewhat improved at 24 hr and 48 hr of incubation, and the rate of improvement at 48 hr of incubation was about 7%. In summary, the glucose uptake ability by the skeletal muscle cell somewhat increases in the presence of EPA.

This result indicates the possibility of somewhat improved glucose uptake ability of the skeletal muscle cell in the patients administered with EPA.

(4) Effects of the Copresence of Statin and EPA

In the statin+EPA group (Statin+EPA), the uptake of the radioactivity is not much different from that of the control group (Cont.) within 6 hr of incubation while the radioactivity uptake considerably decreased at 24 hr and 48 hr of incubation and the rate of decrease at 48 hr of incubation was about 36%. This decrease, however, was smaller compared to the statin group (Statin), and the suppression rate in the presence of the EPA was about 50% of the decrease by the statin. In summary, decrease of the glucose uptake ability by the skeletal muscle cell is suppressed in the presence of the EPA.

It can be elucidated from the results that administration of the EPA to a patient administered with the statin leads to the suppression of the decrease of the glucose uptake ability of the skeletal muscle cell due to the statin, and this in turn suppresses the risk of blood glucose increase. In other words, the results indicate the possibility that the EPA suppresses the increase of the blood glucose due to the statin administration.

The invention claimed is:

1. A method for reducing new incidence rate of diabetes due to administration of HMG-CoA RI comprising the step of administering a pharmaceutical composition containing at least one member selected from the group consisting of eicosapentaenoic acid and its pharmaceutically acceptable salts and esters as its effective component to a patient having a fasting blood glucose at least from 110 mg/dL to less than 126 mg/dL, administered with HMG-CoA RI.

2. A method for suppressing increase of blood glucose due to administration of HMG-CoA RI comprising the step of administering a pharmaceutical composition containing at least one member selected from the group consisting of eicosapentaenoic acid and its pharmaceutically acceptable salts and esters as its effective component to a patient having a fasting blood glucose at least from 110 mg/dL to less than 126 mg/dL, administered with HMG-CoA RI.

3. The method according to claim 1 wherein the patient has a serum HDL cholesterol concentration of less than 40 mg/dL.

4. The method according to claim 1 wherein the patient simultaneously suffers from low HDL cholesterolemia.

5. The method according to claim 3 wherein the patient has a serum triglyceride concentration of at least 150 mg/dL.

6. The method according to claim 3 wherein the patient simultaneously suffers from hypertriglyceridemia.

7. The method according to claim 1 wherein the patient has impaired glucose tolerance or obesity.

8. The method according to claim 1 wherein at least one member selected from the group consisting of eicosapentaenoic acid and its pharmaceutically acceptable salts and esters is ethyl eicosapentate or eicosapentaenoic acid.

9. The method according to claim 2 wherein the patient has a serum HDL cholesterol concentration of less than 40 mg/dL.

10. The method according to claim 2 wherein the patient simultaneously suffers from low HDL cholesterolemia.

11. The method according to claim 9 wherein the patient has a serum triglyceride concentration of at least 150 mg/dL.

12. The method according to claim 9 wherein the patient simultaneously suffers from hypertriglyceridemia.

13. The method according to claim 2 wherein the patient has impaired glucose tolerance or obesity.

14. The method according to claim 2 wherein at least one member selected from the group consisting of eicosapentaenoic acid and its pharmaceutically acceptable salts and esters is ethyl eicosapentate or eicosapentaenoic acid.

* * * * *